(12) United States Patent
Pandya (10) Patent No.: US 11,173,302 B2
(45) Date of Patent: Nov. 16, 2021

(54) NERVE STIMULATION SYSTEM

(71) Applicant: HaloStim, LLC, Savannah, GA (US)

(72) Inventor: Andrew Pandya, Savannah, GA (US)

(73) Assignee: Halostim, LLC, Savannah, GA (US)

(*) Notice: Subject to any disclaimer, the term of this patent is extended or adjusted under 35 U.S.C. 154(b) by 0 days.

(21) Appl. No.: 16/352,088

(22) Filed: Mar. 13, 2019

(65) Prior Publication Data

US 2019/0209840 A1    Jul. 11, 2019

Related U.S. Application Data (63) Continuation of application No. 15/465,416, filed on Mar. 21, 2017, now Pat. No. 10,350,412.

(51) Int. Cl.
| | | |
|---|---|---|
| *A61N 1/36* | (2006.01) | |
| *A61N 1/04* | (2006.01) | |
| *A61M 5/42* | (2006.01) | |

(52) U.S. Cl.
CPC ......... *A61N 1/36021* (2013.01); *A61M 5/422* (2013.01); *A61N 1/0456* (2013.01); *A61N 1/0472* (2013.01); *A61N 1/36034* (2017.08)

(58) Field of Classification Search
CPC ............ A61N 1/36021; A61N 1/36034; A61N 1/0456; A61N 1/0472; A61M 5/422
See application file for complete search history.

(56) References Cited

U.S. PATENT DOCUMENTS

| | | |
|---|---|---|
| 6,071,267 A | 6/2000 | Zamierowski |
| 2004/0138602 A1 | 7/2004 | Rossen |
| 2009/0127935 A1 | 9/2009 | Zanella et al. |
| 2013/0325097 A1 | 12/2013 | Loest |
| 2014/0358058 A1 | 12/2014 | Nelson |
| 2016/0081580 A1 | 3/2016 | Bergelin et al. |
| 2016/0213521 A1 | 7/2016 | Bacon et al. |
| 2017/0209693 A1* | 7/2017 | An .................... A61N 1/36034 |

FOREIGN PATENT DOCUMENTS

WO    2017/009130    1/2017

OTHER PUBLICATIONS

U.S. Appl. No. 15/785,229; Office Action dated Jan. 9, 2019.
PCT International Patent Application No. PCT/US18/22151; International Search Report and Written Opinion of the International Searching Authority dated Aug. 3, 2018, 12 pages.
U.S. Appl. No. 15/465,416, filed Mar. 21, 2017.
GF Health Products, Inc., Transcutaneous Electrical Nerve Stimulation Device LUMI-TENS, Operation Manual, 2008, 12 total pages, GF Health Products, Inc.

* cited by examiner

*Primary Examiner* — Lindsey G Wehrheim
(74) *Attorney, Agent, or Firm* — Craig R. Miles; CR Miles P.C.

(57) ABSTRACT

A nerve stimulation system including one or more of an annular frame, an electrically conductive element disposed in the annular frame, and a controller electrically coupled to the electrically conductive element and a power source.

15 Claims, 11 Drawing Sheets

NERVE STIMULATION SYSTEM

This United States Patent Application is a continuation of U.S. patent application Ser. No. 15/465,416, filed Mar. 21, 2017, hereby incorporated by reference herein.

I. FIELD OF THE INVENTION

A nerve stimulation system including one or more of an annular frame, an electrically conductive element disposed in the annular frame and a controller electrically coupled to the electrically conductive element and a power source.

II. BACKGROUND OF THE INVENTION

The use of hypodermic needles for medical treatment, such as drug administration and blood sampling, is one aspect of treatment in modern medicine. However, while these procedures promote health, the pain associated with hypodermic needle use often causes patients anxiety in seeking or continuing treatment involving hypodermic needles due to the pain associated with the act of injection. Thus, there would be an advantage in a nerve stimulation system operable to decrease pain associated with hypodermic needle injections.

One form of nerve stimulation to reduce pain is transcutaneous electrical nerve stimulation. Certain embodiments of systems which can perform transcutaneous electrical nerve stimulation include electrodes which deliver electrical stimulus to a targeting portion of a patient's body. In use, transcutaneous electrical nerve stimulation operates by gate control theory. At its most basic, this theory is founded upon a principal of "gates" within the spinal cord which operate to control whether pain signals are transmitted to the brain. The "gates" are open when pain is experienced. Changing the nerve signal to the spinal cord using transcutaneous electrical nerve stimulation alters the signal to the "gate", so that the "gate" closes and no longer allows the pain signal to travel to the brain, so that pain is no longer perceived.

III. SUMMARY OF THE INVENTION

Accordingly, one broad object of the present invention is to provide a nerve stimulation system including one or more of: an annular frame having a non-electrically conductive top surface and an electrically conductive bottom surface disposed between an outer annular wall and an inner annular wall defining a frame aperture communicating between the non-electrically conductive top surface and the electrically conductive bottom surface, an annular frame channel disposed in the annular frame, and an electrically conductive element disposed in the annular frame channel, a power source electrically coupled to the electrically conductive element, and a controller including a processor communicatively coupled to a memory element, the memory element containing a program executable to switchably electrically connect and disconnect the power source from the electrically conductive element.

Another broad object of the present invention is to provide a method of making a nerve stimulation system including one or more of: producing a annular frame having a non-electrically conductive top surface and an electrically conductive bottom surface disposed between an outer annular wall and an inner annular wall defining a frame aperture communicating between the non-electrically conductive top surface and the electrically conductive bottom surface, an annular frame channel disposed in the annular frame, disposing an electrically conductive element in the annular frame channel, electrically coupling a power source to the electrically conductive element, and coupling a controller to the power source including a processor communicatively coupled to a memory element containing a program executable to and disconnect the power source from the electrically conductive element.

Another broad object of the present invention is to provide a method of using a nerve stimulation system including one or more of: obtaining a nerve stimulation system including one or more of: obtaining an annular frame having a non-electrically conductive top surface and an electrically conductive bottom surface disposed between an outer annular wall and an inner annular wall defining a frame aperture communicating between the non-electrically conductive top surface and the electrically conductive bottom surface, an annular frame channel disposed in the annular frame, and an electrically conductive element disposed in the annular frame channel, a power source electrically coupled to the electrically conductive element, and a controller including a processor communicatively coupled to a memory element, the memory element containing a program executable to switchably electrically connect and disconnect the power source from the electrically conductive element, disposing the frame aperture about a portion of the dermis of a body, executing the program to switchably electrically connect and disconnect the power source from the electrically conductive element; decreasing a perceived level of pain within the area of the frame aperture defined by the inner annular wall of the annular frame.

Naturally, further objects of the invention are disclosed throughout other areas of the specification, drawings, photographs, and claims.

V. DETAILED DESCRIPTION OF THE INVENTION

Generally referring to FIGS. 1 through 12, a nerve stimulation system (1) can include one or more of an annular frame (2), an electrically conductive element (3), a power source (4), and a controller (5). The annular frame (2) can have a non-electrically conductive top surface (6) and an electrically conductive bottom surface (7) extending between an inner annular wall (8) and an outer annular wall (9). The inner annular wall (8) can define an annular frame aperture (10) communicating between the non-electrically conductive top surface (6) and the electrically conductive bottom surface (7) of the annular frame (2). The non-electrically conductive top surface (6) can be a non-electrically conductive material, as illustrative examples: plastic, a fabric such as cotton, wool, or linen, or combinations thereof. The electrically conductive bottom surface (7) can be an electrically conductive material (12) capable of conducting current (13), as illustrative examples: carbonized silicone rubber, carbon impregnated plastic, conductive carbon film or gel, hydrogel layers, or combination thereof. The non-electrically conductive top surface (6) and the electrically conductive bottom surface (7) can extend from the inner annular wall (8) to the outer annular wall (9). While the Figures show, the inner annular wall (8) and the outer annular wall (9) generally orthogonal to the non-electrically conductive top surface (6) and electrically conductive bottom surface (7); this is not intended to preclude, embodiments in which one or both of the inner annular wall (8) or the outer annular wall (9) can be disposed at an angle or in arcuate relation to the non-electrically conductive top surface (6) and electrically conductive bottom surface (7).

Figure 2:
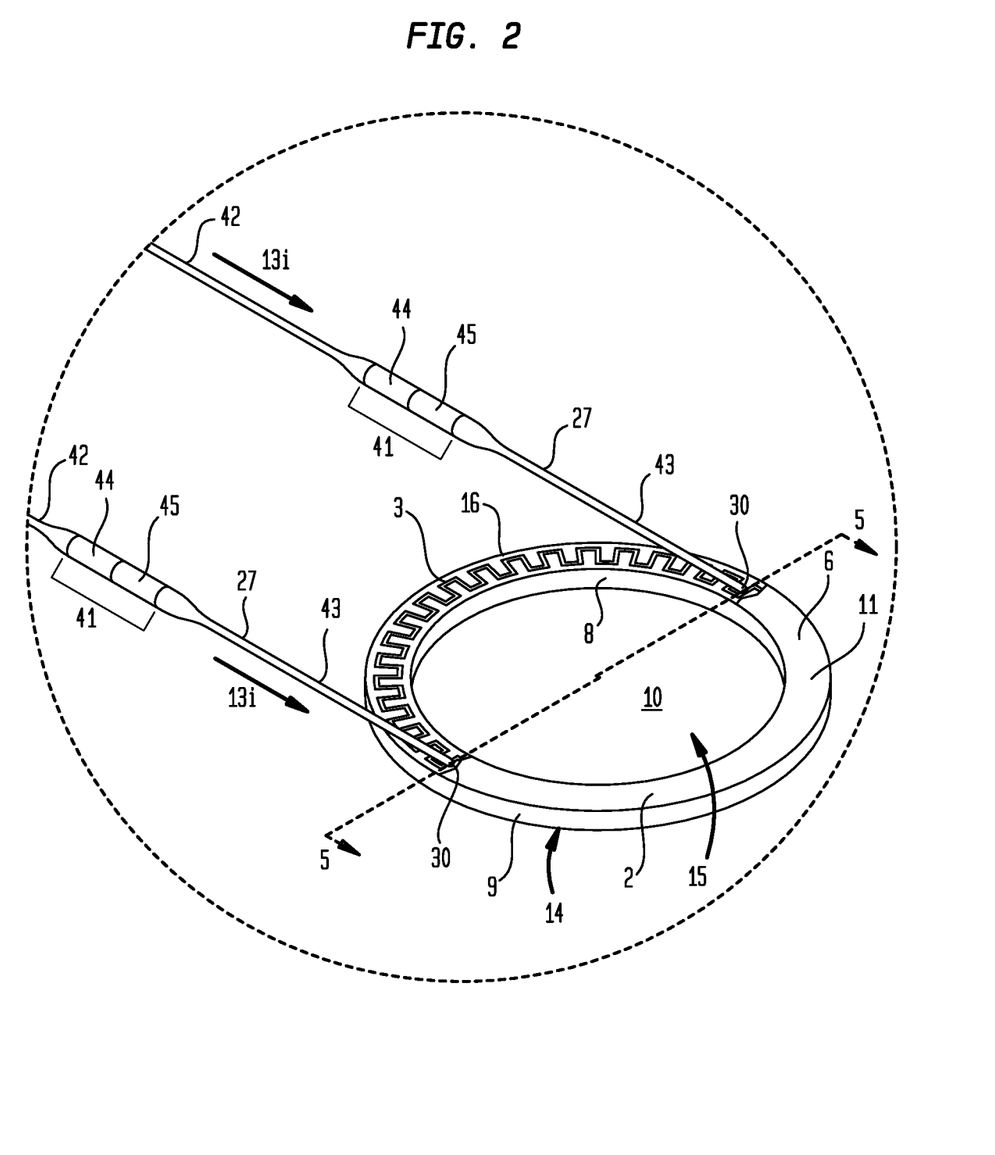
FIG. 2 is an enlarged view of a particular embodiment of an annular frame.

In particular embodiments, the annular frame (2) can have generally circular (14) inner and outer annular walls (8)(9) with the inner annular wall (8) defining a circular frame aperture (15) (as shown in the example of FIG. 2). However, this is not intended to preclude embodiments in which the annular frame (2) defines a square, rectangle, diamond, triangle, or other geometric shape having a continuous perimeter, and having an inner annular wall (8) correspondingly defining a frame aperture (10) configured as a square, rectangle, or other geometric shape.

Now referring primarily to FIGS. 2 through 5, in particular embodiments, the annular frame (2) can have an annular frame channel (16) disposed between the inner annular wall (8) and the outer annular wall (9) and between the non-electrically conductive top surface (6) and the electrically conductive bottom surface (7), and electrically connected to the electrically conductive bottom surface (7). An electrically conductive element (3) can be disposed in the annular frame channel (16).

Figure 3:
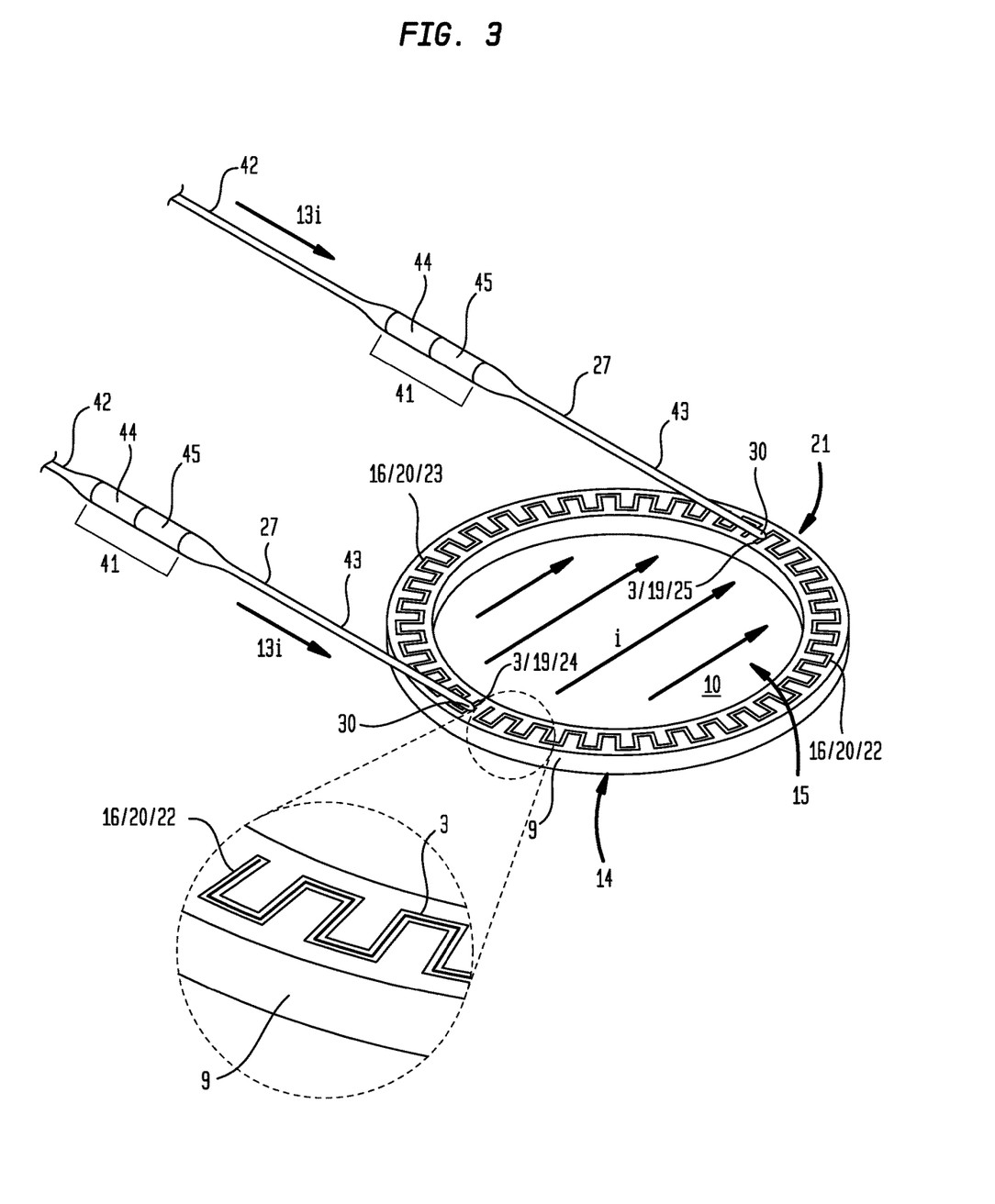
FIG. 3 is an enlarged view of a particular embodiment of an annular frame.
Figure 4:
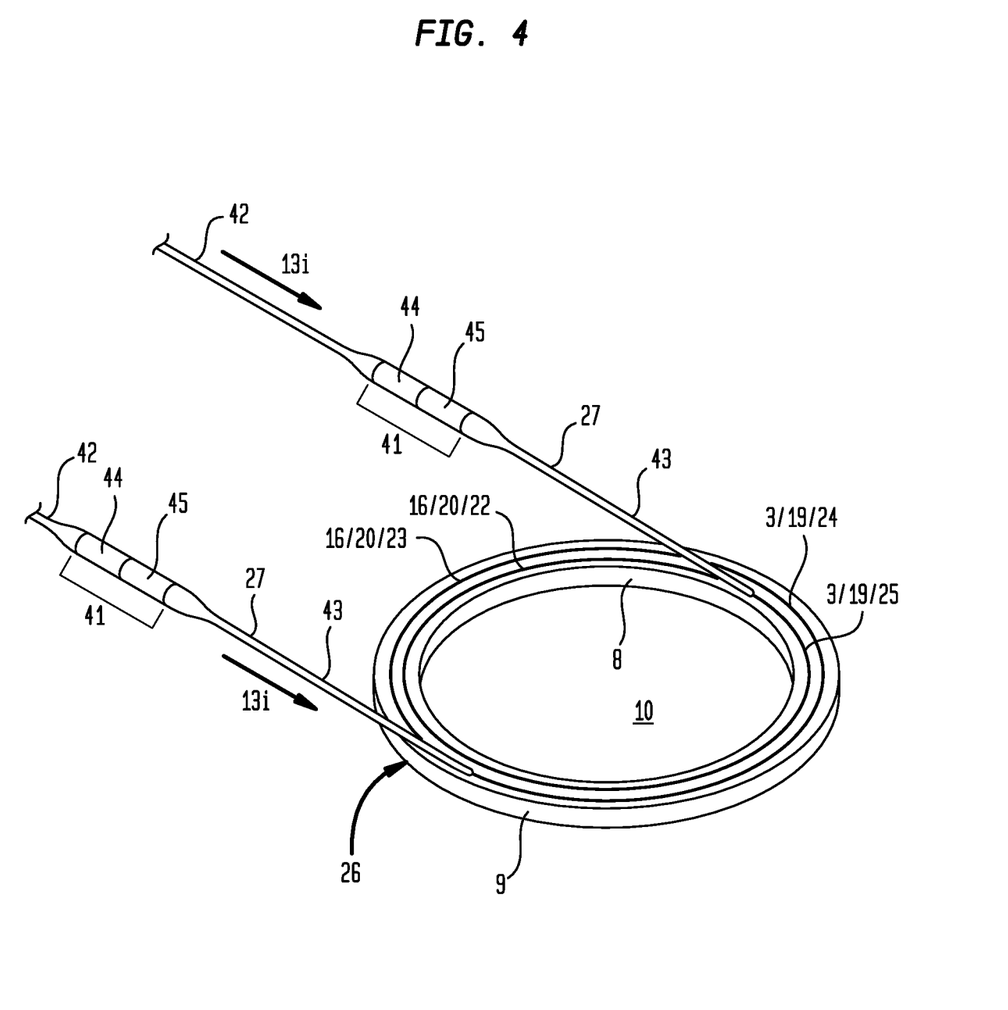
FIG. 4 is an enlarged view of a particular embodiment of an annular frame.
Figure 5:
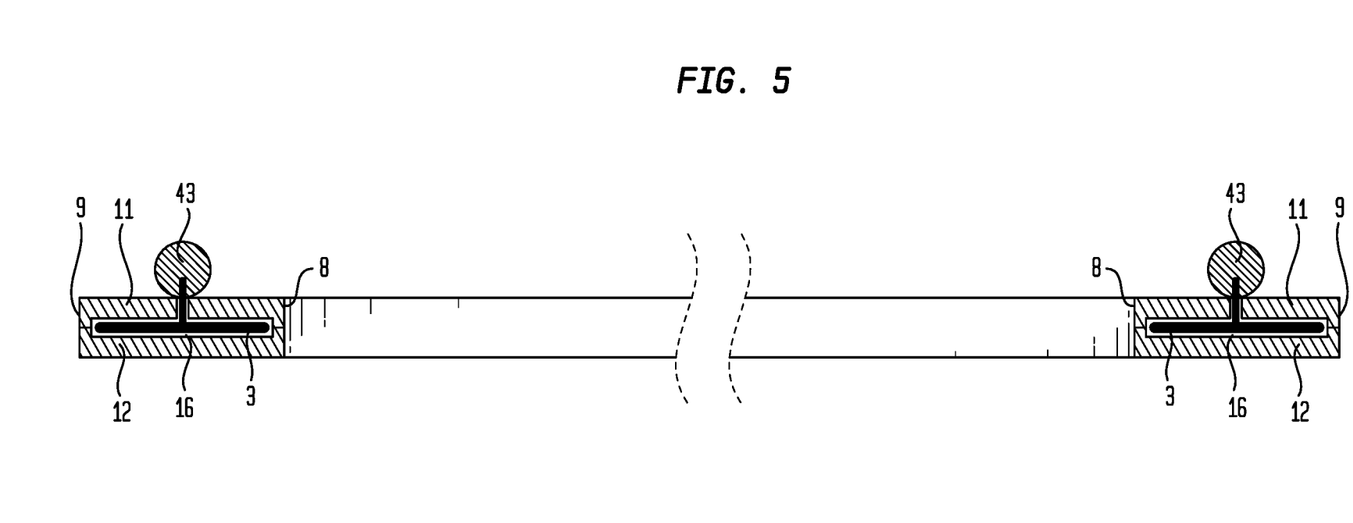
FIG. 5 is a cross-sectional view 5-5 of a particular embodiment of an annular frame as shown in FIG. 2.

Now referring primarily to FIGS. 3 and 4, in particular embodiments, the electrically conductive element (3) can comprise a plurality of discrete electrically conductive elements (19) each correspondingly disposed in a plurality of discrete annular frame channels (20).

Referring now to FIG. 3, a first annular frame channel (22) can be disposed in opposite relation to a second annular frame channel (23) between a non-electrically conductive top surface (6) and an electrically conductive bottom surface (7) in a first configuration (21). A first electrically conductive element (24) and a second electrically conductive element (25) can be corresponding disposed in the first and second annular frame channels (22)(23). The power source (4) can be discretely connected to each of the first and second electrically conductive elements (24)(25).

Referring now to FIG. 4, a plurality of discrete electrically conducting elements (19) can be disposed in a plurality of discrete annular frame channels (20) in a second configuration (26). A first annular frame channel (22) and a second annular frame channel (23) can be circumferentially disposed in parallel relation a distance apart between a non-electrically conductive top surface (6) and an electrically conductive bottom surface (7). A first electrically conductive element (24) and a second electrically conductive element (25) can be correspondingly disposed in a first annular frame channel (22) and a second annular frame channel (23). The power source (4) can be discretely connected to each of the first and second electrically conductive elements (24)(25).

The electrically conductive element (3) can comprise a wide variety of materials capable of conducting a current (13) including or consisting of: copper, silver, gold, beryllium copper, phosphor bronze, zirconium copper, constantan, MANGANIN, nickel, steel, or combinations thereof.

Figure 13:
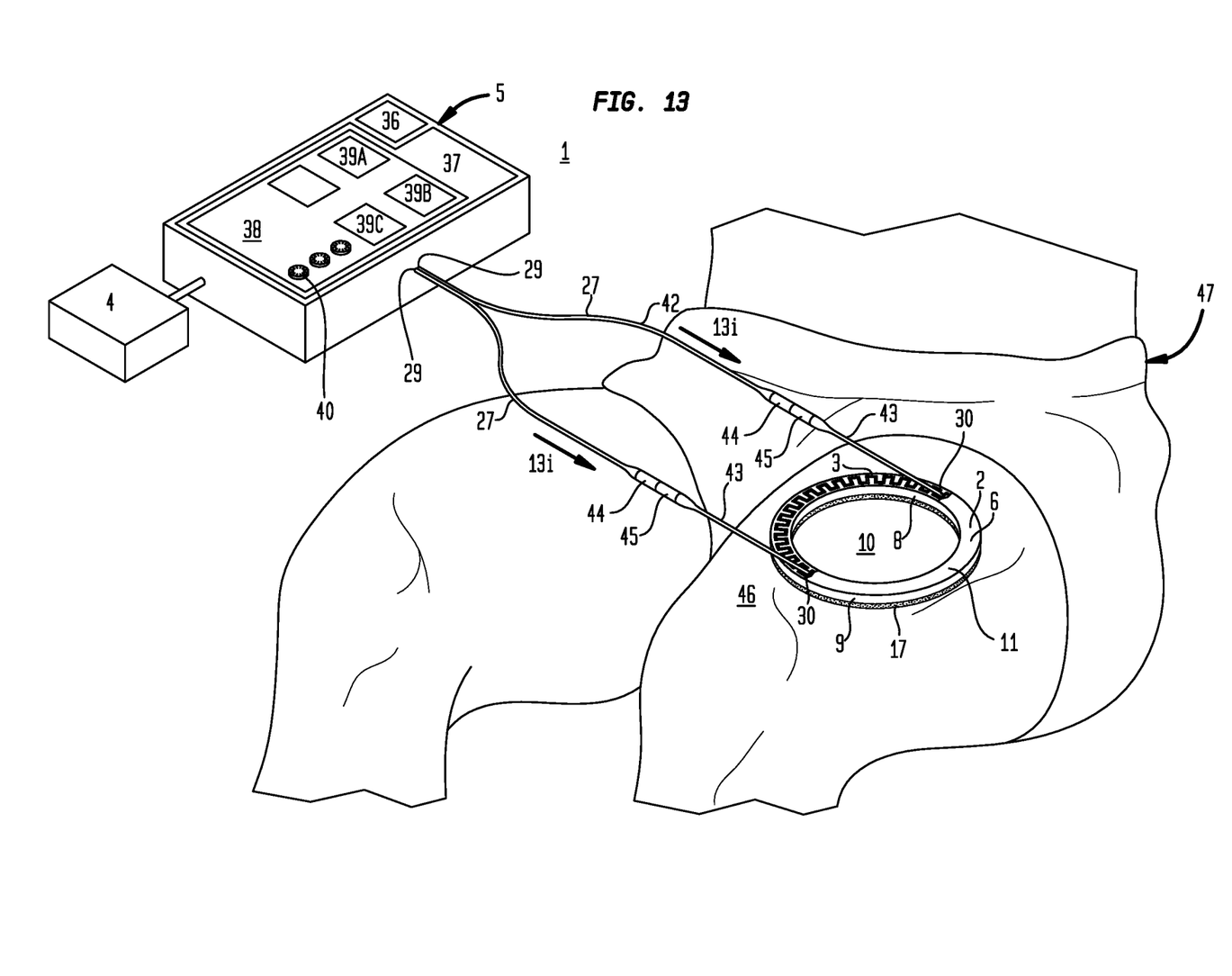
FIG. 13 is a perspective view illustrating a method of using a particular embodiment of a nerve stimulation system.

Now referring primarily to FIG. 13, particular embodiments of the nerve stimulation system (1) can, but need not necessarily, include an adhesion layer (17) coupled to the electrically conductive bottom surface (7) of the annular frame (2). The adhesion layer (17) can comprise a pressure sensitive or wet adhesion layer. A pressure sensitive adhesive can be described as a viscous and tacky material capable of wetting a surface on contact, which bonds with the contact surface with the application of pressure. The material comprising the pressure sensitive adhesive can be rubber-based, acrylic-based, silicone-based, or other like material, or combinations thereof. A wet adhesion layer can be described as a viscous gel or other conductive liquid medium that operates to facilitate the transfer of current (13) from the conducting material to the object receiving the current (13). In further particular embodiments, the adhesion layer (17) can be capable of increasing, decreasing, or maintaining the strength of the current (13) generated by the electrically conductive element (3). The capability of the adhesion layer (17) to manipulate the strength of the current (13) can be obtained by the addition of an impurity to the materials comprising the adhesion layer (17), where the impurity alters the conduction characteristics of the adhesion layer (17)

Now referring primarily to FIGS. 1 and 6 through 12, a nerve stimulation system (1) can include a power source (4). The power source (4) can be electrically coupled to the electrically conductive element (3) and capable of generating a current (13) to and through the electrically conductive element (3). In particular embodiments, the power source (4) can comprise a direct current source such as a battery or an alternating current source such as a 120 volt outlet with an alternating current adapter coupled to an electrical outlet to convert the alternating current to direct current, or other like electrical power source (4), or combinations thereof.

In particular embodiments of a nerve stimulation system (1), the power source (4) can be electrically coupled to the electrically conductive element (3) by utilizing a plurality of leadwires (27). Each of the one or more leadwires (27) can have a length (28) disposed between a leadwire first end (29) and a leadwire second end (30). In particular embodiments, coupling of each of the plurality of leadwires (27) can be achieved by configuring the leadwire first end (29) as a male or female connector (31)(32) which can be insertingly engaged to a complementary male or female connector (31)(32) disposed on the controller (5) and the leadwire second end (30) can be integrated to the electrically conductive element (3). In other particular embodiments, the leadwire first end (29) can be integrated with the controller (5) and the leadwire second end (30) can be configured as a male or female connector (31)(32) which can be insertingly engaged to a complementary male or female connector (31)(32) disposed on the electrically conductive element (3).

In other particular embodiments, the leadwire first end (29) can be integrated to the controller (5) and the leadwire second end (30) can be integrated to the electrically conductive element (3). In other particular embodiments the leadwire first end (29) can be configured as a male or female connector (31)(32) and insertingly engaged to a complementary male or female connector (31)(32) disposed on the controller (5) and the leadwire second end (30) can be configured as a male or female connector (31)(32) which can be insertingly engaged to a complementary male or female connector (31)(32) disposed on the electrically conductive element (3). Each of the plurality of leadwires (27) can be coupled to the controller (5) and the electrically conductive element (3) by utilizing the same configuration or combination of configurations described above.

For purposes of this invention, the term female connector (32) means a connector (33) attached to a leadwire (27) having one or more recessed holes (34) with electrical terminals (35) inside configured to accept a male connector (31), and the term male connector (31) means a connector (33) having exposed electrical terminal(s) (35) and configured to be received in a female connector (32). The leadwire (27) can be comprised of a leadwire conducting material encased within a non-conducting material. The leadwire conducting material can include or consist of: copper, a copper alloy, tinsel wire, silver, gold, or other like conducting material, or combinations thereof. The non-conducting material can include or consist of: silicone, polyvinyl chloride, thermoplastic elastomer, thermoplastic rubber, thermoplastic polyurethane, or other like non-conducting material.

Figure 1:
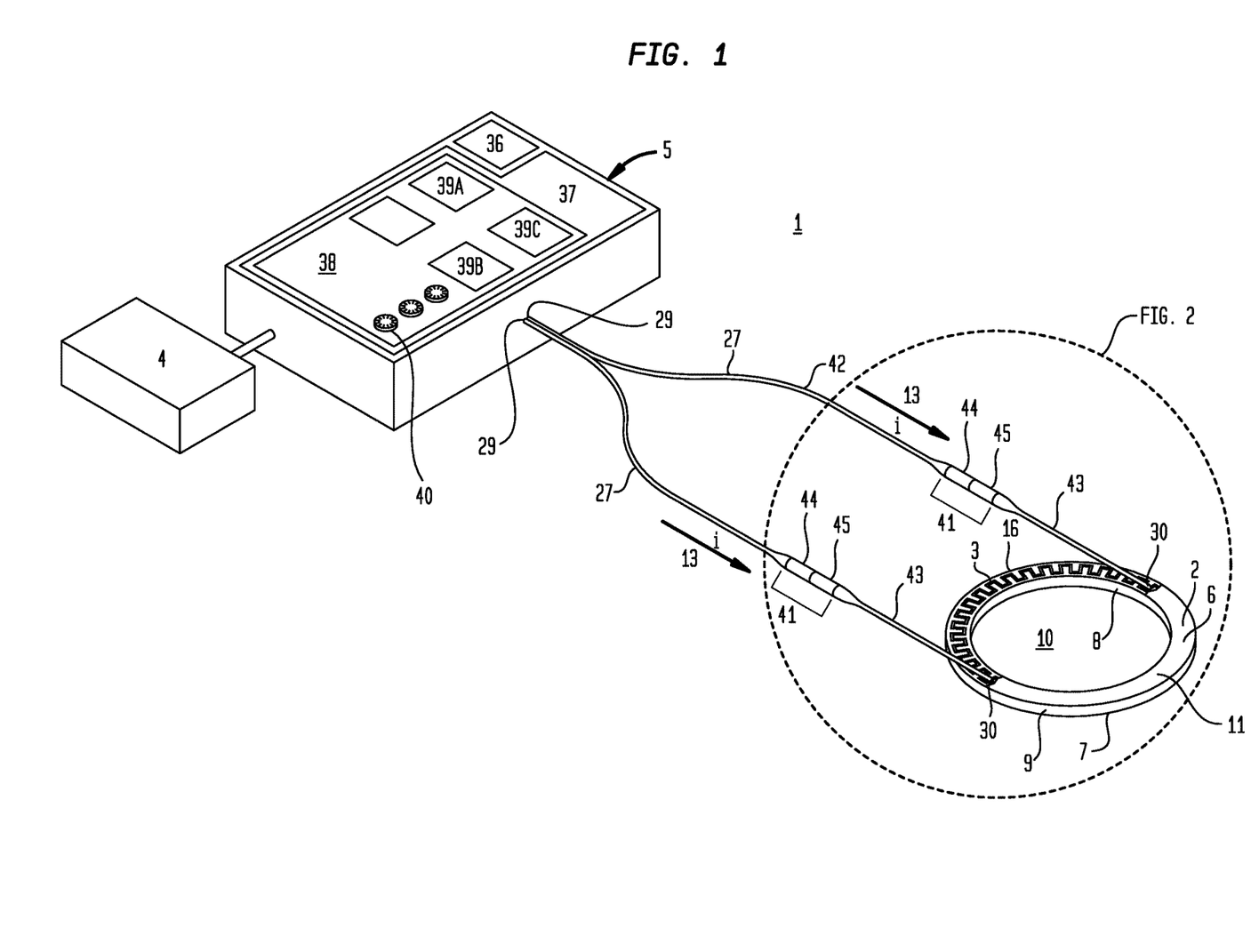
FIG. 1 is a perspective view of a particular embodiment of a nerve stimulation system.

Now referring primarily to FIGS. 1 and 6 through 12, the nerve stimulation system (1) can include a controller (5). The controller (5) can be electrically coupled to the power source (4) and the electrically conductive element (3). In particular embodiments, the power source (4) can be integrated into the controller (5) as a single unit electrically coupled to the electrically conductive element (3), or the power source (4) can be externally electrically coupled to the controller (5), which can be electrically coupled to the electrically conductive element (3) (as shown in FIG. 1). The controller (5) can further include a processor (36) communicatively coupled to a memory element (37) containing a program (38) executable to periodically electrically couple or uncouple the power source (4) to or from the electrically conductive element (3).

In particular embodiments, the program (38) can include a current regulation module (39A) executable to electrically couple the power source (4) to the electrically conductive element (3) to deliver a current (13) between about 0 mA to about 100 mA. In particular embodiments, the current (13) can be selected from the group including or consisting of: about 1 milliamp ("mA") to about 10 mA, about 5 mA to about 15 mA, about 10 mA to about 20 mA, about 15 mA to about 25 mA, about 20 mA to about 30 mA, about 25 mA to about 35 mA, about 30 mA to about 40 mA, about 35 mA to about 45 mA, about 40 mA to about 50 mA, about 45 mA to about 55 mA, about 50 mA to about 60 mA, about 55 mA to about 65 mA, about 60 mA to about 70 mA, about 65 mA to about 75 mA, about 70 mA to about 80 mA, about 75 mA to about 85 mA, about 80 mA to about 90 mA, about 85 mA to about 95 mA, and about 90 mA to about 99 mA, or combinations thereof.

In further particular embodiments, the program (38) can further include a pulse rate generator (39B) executable to electrically couple and uncouple the power source (4) to and from the electrically conductive element (3) at a current pulse rate. For purposes of this invention, the term current pulse rate means the number of times the power source (4) electrically couples and uncouples to and from the electrically conductive element (3) over a duration of time. The current pulse rate can be between about 1 pulse per second ("pps") to about 250 pulses per second. In further particular embodiments, the current pulse rate can be selected from the group consisting of about 5 pps to about 20 pps, about 10 pps to about 30 pps, about 20 pps to about 40 pps, about 30 pps to about 50 pps, about 40 pps to about 60 pps, about 50 pps to about 70 pps, about 60 pps to about 80 pps, about 70 pps to about 90 pps, about 80 pps to about 100 pps, about 90 pps to about 110 pps, about 100 pps to about 120 pps, about 110 pps to about 130 pps, about 120 pps to about 140 pps, about 130 pps to about 150 pps, about 140 pps to about 160 pps, about 150 pps to about 170 pps, about 160 pps to about 180 pps, about 170 pps to about 190 pps, about 180 pps to about 200 pps, about 210 pps to about 230 pps, about 220 pps to about 240 pps, and about 230 pps to about 245 pps, or combinations thereof.

In further particular embodiments, the program (38) can further include a pulse width generator (39C) that can be executable to electrically couple and uncouple the power source (4) to and from the electrically conductive element (3) at a current pulse width between about 1 millisecond ("ms") to about 250 ms. In further particular embodiments, the current pulse width can be selected from the group consisting of about 5 ms to about 20 ms, about 10 ms to about 30 ms, about 20 ms to about 40 ms, about 30 ms to about 50 ms, about 40 ms to about 60 ms, about 50 ms to about 70 ms, about 60 ms to about 80 ms, about 70 ms to about 90 ms, about 80 ms to about 100 ms, about 90 ms to about 110 ms, about 100 ms to about 120 ms, about 110 ms to about 130 ms, about 120 ms to about 140 ms, about 130 ms to about 150 ms, about 140 ms to about 160 ms, about 150 ms to about 170 ms, about 160 ms to about 180 ms, about 170 ms to about 190 ms, about 180 ms to about 200 ms, about 210 ms to about 230 ms, about 220 ms to about 240 ms, and about 230 ms to about 245 ms, or combinations thereof.

In particular embodiments, the controller (5) can further include an interface (40) operable by a user of the nerve stimulation system (1). The interface (40) can enable a user to select a current (13), current pulse rate, and a pulse width. The interface (40) can be a graphical interface, such as a push-button interface, touch screen, or other like graphical interface. The interface (40) can also be a series of marked dials maneuverable by the user to make a selection.

Figure 6:
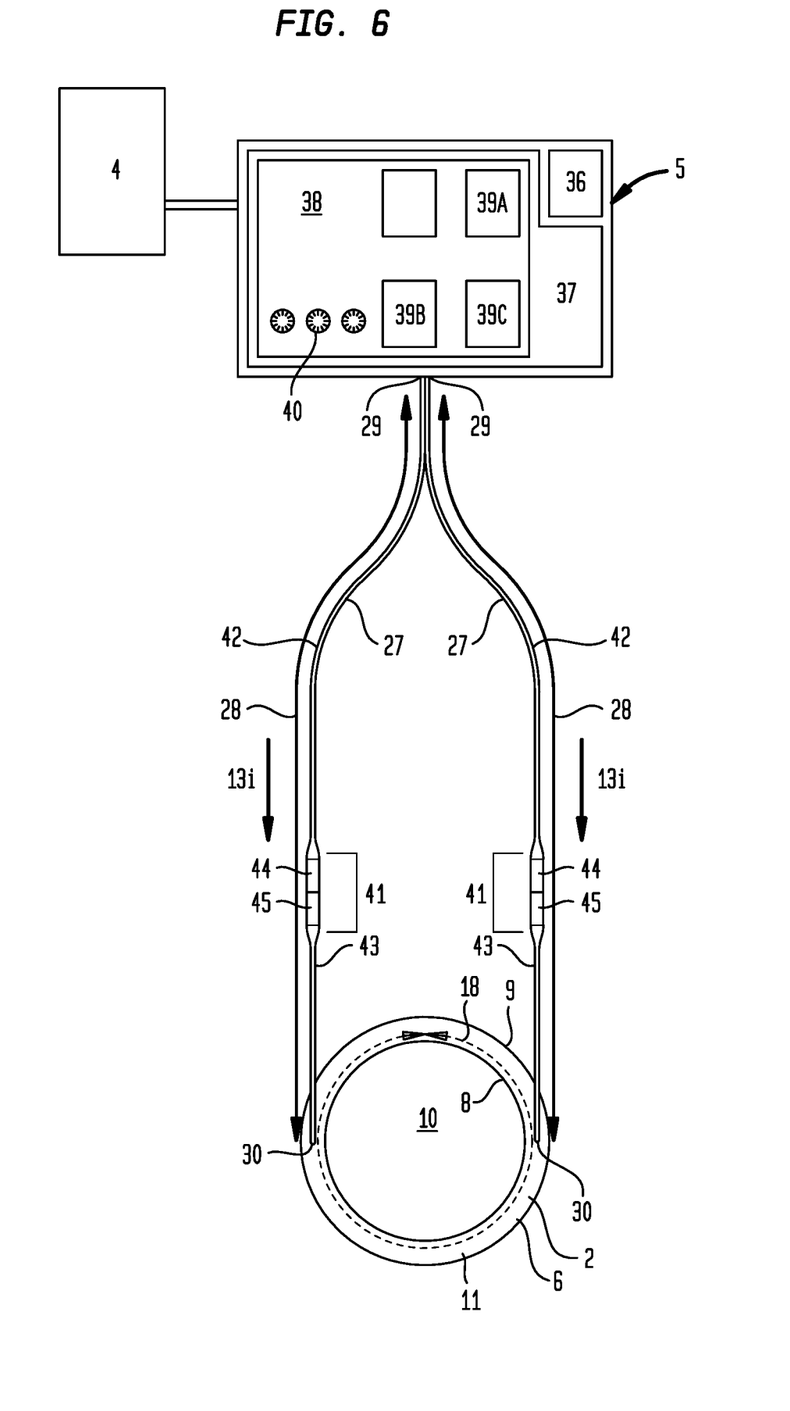
FIG. 6 is a top plan view of a particular embodiment of a nerve stimulation system.
Figure 7:
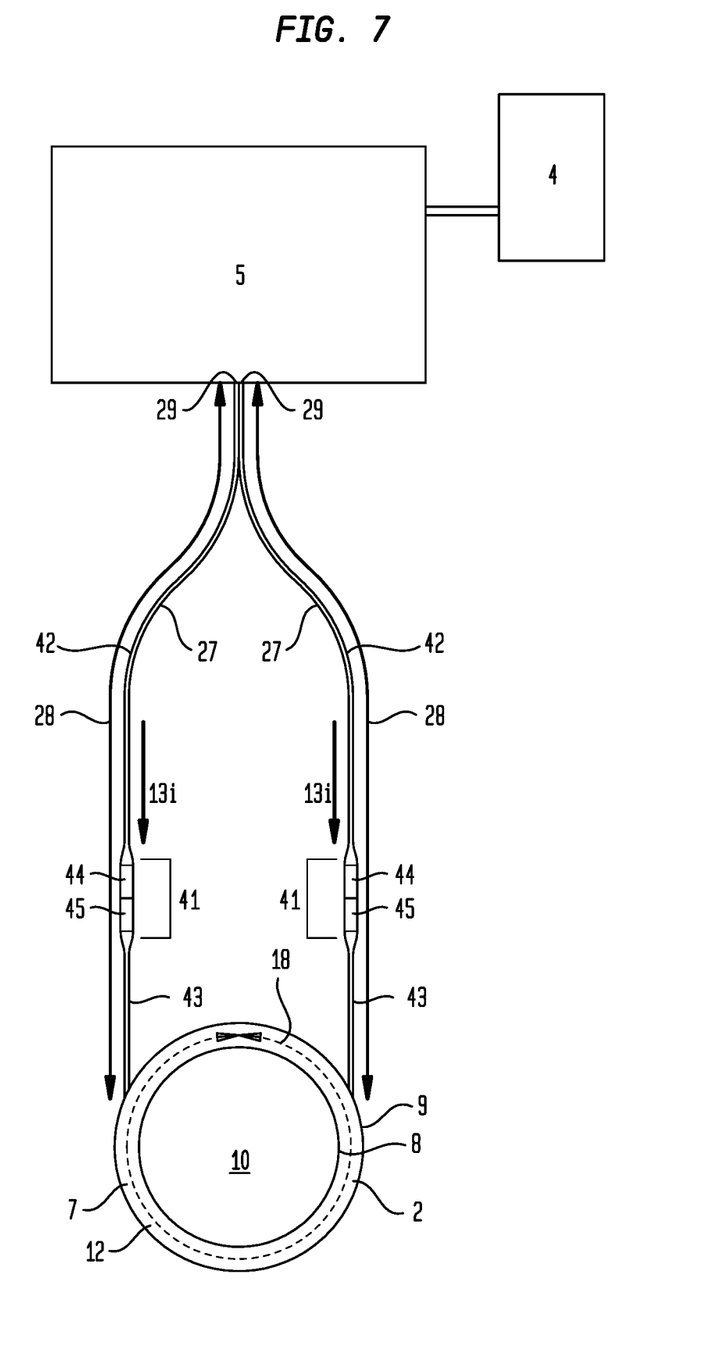
FIG. 7 is a bottom plan view of a particular embodiment of a nerve stimulation system.
Figure 8:
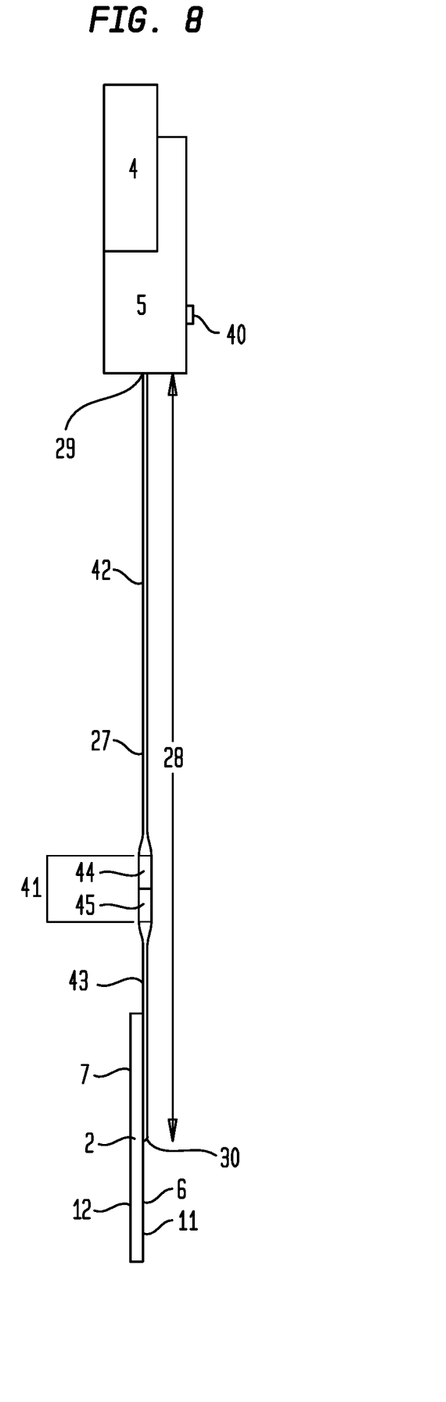
FIG. 8 is a first side elevation view of a particular embodiment of a nerve stimulation system.
Figure 9:
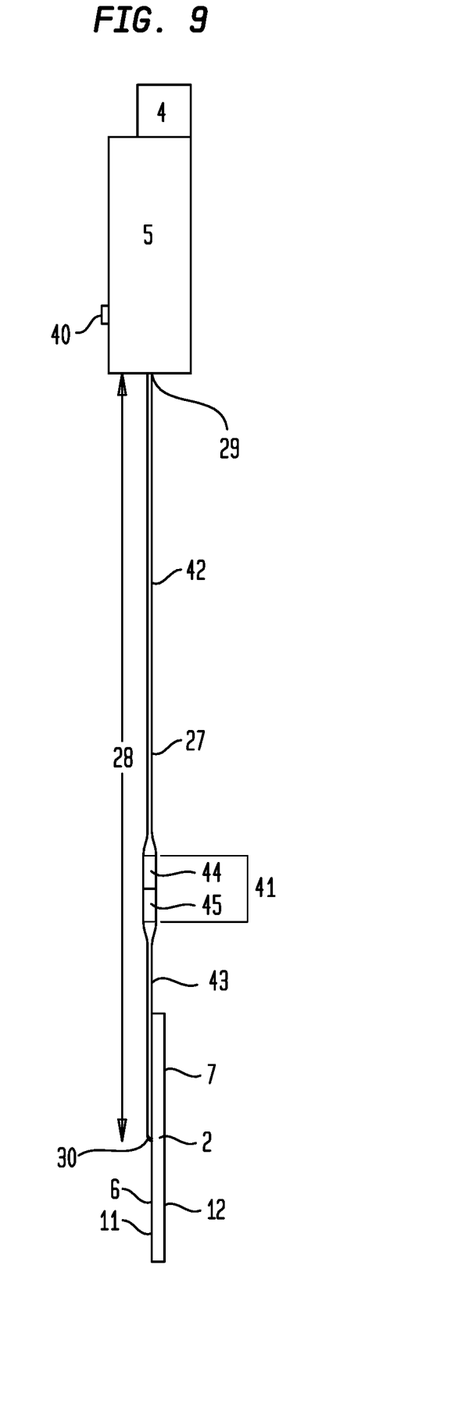
FIG. 9 is second side elevation view of a particular embodiment of a nerve stimulation system.
Figure 10:
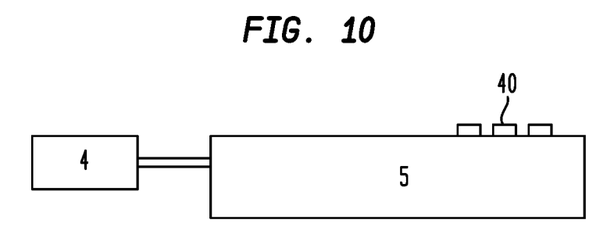
FIG. 10 is a front elevation view of a particular embodiment of a nerve stimulation system.
Figure 11:
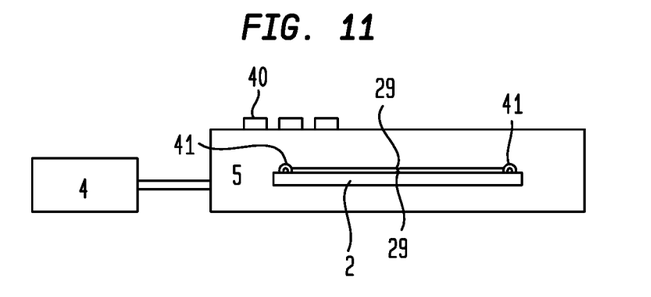
FIG. 11 is a back elevation view of a particular embodiment of a nerve stimulation system.
Figure 12:
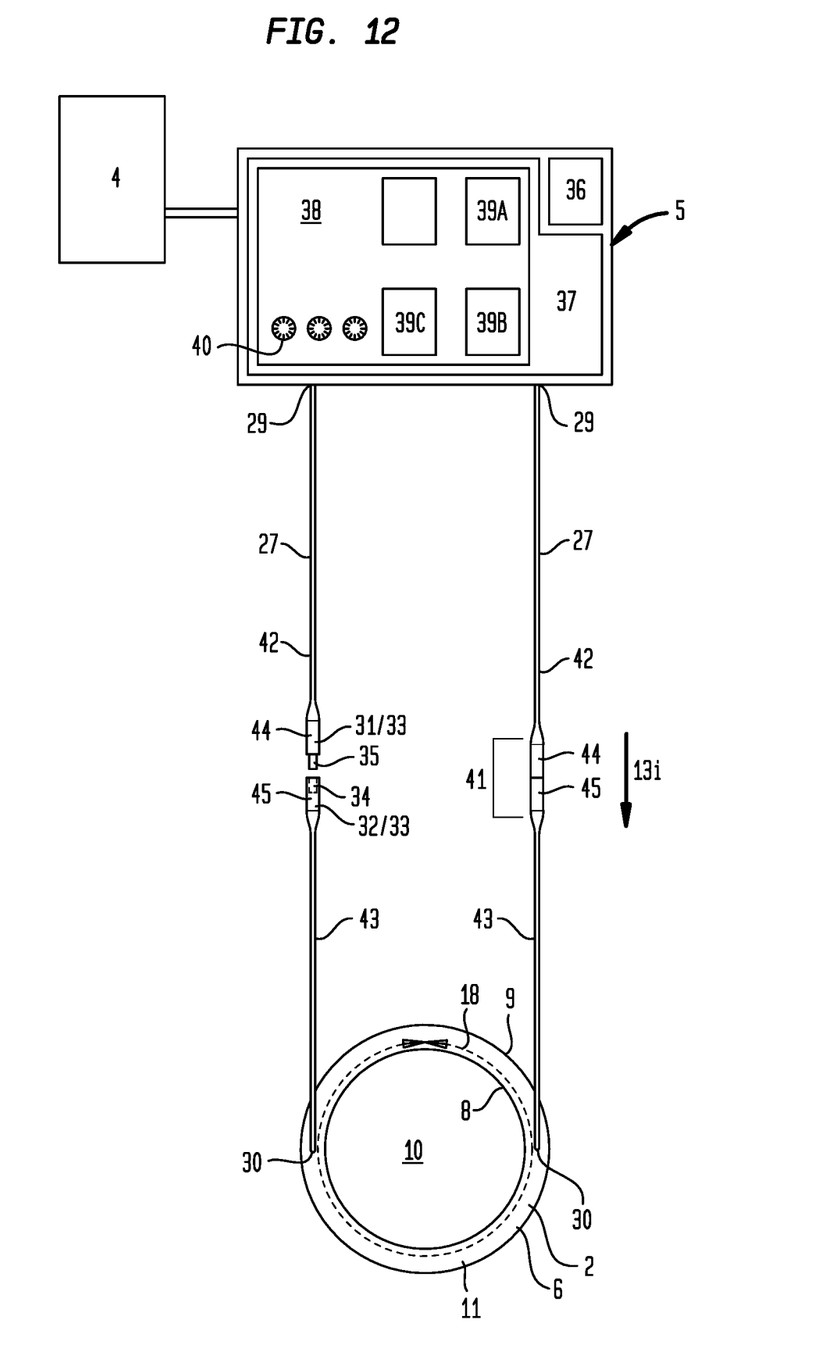
FIG. 12 is a top plan view of a particular embodiment of a nerve stimulation system.

Now referring primarily to FIGS. 6 and 12, particular embodiments of the nerve stimulation system (1) can include one or more breaker elements (41). A breaker element (41) can be disposed at a location along the length (28) of the leadwire (27) between the leadwire first end (29) and the leadwire second end (30) to define a leadwire first portion (42) coupled to the controller (5) and a leadwire second portion (43) coupled to the electrically conductive element (3). The breaker element (41) can be configured to have a first connector (44) and a second connector (45) capable of electrically coupling and uncoupling the electrically conductive element (3) and the power source (4) along the length (28) of the leadwire (27) by matingly engaging or disengaging the first connector (44) and second connector (45) of the breaker element (41). As an illustrative example, FIG. 6 shows the flow of current (13) through a nerve stimulation system (1) when the first connector (44) and second connector (45) of the breaker element (41) is matingly engaged. FIG. 12 shows the flow of current (13) through a nerve stimulation system (1) when the first connector (44) and second connector (45) of the breaker element (41) is not matingly engaged. The breaker element (41) can be utilized to rapidly disrupt the operation of the nerve stimulation system (1) by matingly disengaging the first connector (44) and second connector (45) to interrupt the electrical coupling of the power source (4) and the electrically conductive element (3).

Now referring generally to FIG. 13, methods of using particular embodiments of the nerve stimulation system (1) can include one or more of obtaining a nerve stimulation system (1), which includes one or more of an annular frame (2), an electrically conductive element (3), a power source (4), and a controller (5), disposing a frame aperture (10) about a portion of a dermis (46) of a body (47), selecting a program (38) contained on the memory element (37) communicatively coupled to the processor (36) of the controller (5), and executing the program (38) to cause a current (13) to emit from the power source (4) to the electrically conductive element (3); the annular frame (2), electrically conductive element (3), power source (4), and controller (5) being described above. In further particular embodiments of using the nerve stimulation system (1), the program (38) can be executed to periodically couple or uncouple the power source (4) from the electrically conductive element (3) at a current (13), a current pulse rate, a current pulse width, or combination thereof, as described above. In particular embodiments having an adhesion layer (17) coupled to the bottom surface (7) of the annular frame (2), a method of using the nerve stimulation system (1) can also include coupling and uncoupling the adhesion layer (17) to the dermis (46) to spatially position the annular frame (2) over a portion of the dermis (46).

As can be easily understood from the foregoing, the basic concepts of the present invention may be embodied in a variety of ways. The invention involves numerous and varied embodiments of a nerve stimulation system and methods for making and using such a nerve stimulation system, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "electrically conductive element" should be understood to encompass disclosure of the act of "conducting"—whether explicitly discussed or not—and, conversely, were there effectively disclosure of the act of "conducting", such a disclosure should be understood to encompass disclosure of a "electrically conductive element" and even a "means for conducting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the nerve stimulation systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A nerve stimulation system, comprising:
   an annular frame having a non-electrically conductive top surface opposite an electrically conductive bottom surface, each of said non-electrically conductive top surface and said electrically conductive bottom surface extending between an inner annular wall and an outer annular wall, said inner annular wall defining a frame aperture open to said non-electrically conductive top surface and said electrically conductive bottom surface of said annular frame;
   an annular frame channel circumferentially disposed in said annular frame between said non-electrically conductive top surface and said electrically conductive bottom surface; and
   an electrically conductive element disposed in said annular frame channel, said electrically conductive element electrically connected to said electrically conductive bottom surface of said annular frame.

2. The nerve stimulation system of claim 1, further comprising an adhesion layer disposed on said electrically conductive surface of said annular frame, said adhesion layer capable of removably coupling said annular frame to an anatomical surface.

3. The nerve stimulation system of claim 1, wherein said annular frame channel comprises a first annular frame channel and a second annular frame channel circumferentially disposed in parallel relation a distance apart between said non-electrically conductive surface and said electrically conductive surface, wherein said electrically conductive element comprises a first electrically conductive element and a second electrically conductive element, each of said first and second electrically conductive elements disposed within a corresponding one of said first and second annular frame channels, each of said first and second electrically conductive elements discretely coupled to a power source.

4. The nerve stimulation system of claim 1, wherein said annular frame channel comprises a first annular frame channel disposed in opposite relation to a second annular frame channel between said non-electrically conductive surface and said electrically conductive surface, wherein said electrically conductive element comprises a first electrically conductive element and a second electrically conductive element, each of said first and second electrically conductive elements disposed within a corresponding one of said first and second annular frame channels, each of said first and second electrically conductive elements discretely coupled to said power source.

5. A nerve stimulation system, comprising:
   an annular frame having a non-electrically conductive surface opposite an electrically conductive surface, each of said non-electrically conductive surface and said electrically conductive surface extending between an inner annular wall and an outer annular wall, said inner annular wall defining a frame aperture communicating between said non-electrically conductive surface and said electrically conductive surface of said annular frame; and
   an annular frame channel circumferentially disposed in said annular frame between said non-electrically conductive surface and said electrically conductive surface; and
   an electrically conductive element disposed in said annular frame channel, said electrically conductive element electrically connected to said electrically conductive surface, wherein said electrically conductive element selected from the group consisting of: copper, silver, gold, beryllium copper, phosphor bronze, zirconium copper, constantan, manganin, nickel, steel, or combinations thereof.

6. A nerve stimulation system, comprising:
   an annular frame having a non-electrically conductive surface opposite an electrically conductive surface, each of said non-electrically conductive surface and said electrically conductive surface extending between an inner annular wall and an outer annular wall, said inner annular wall defining a frame aperture communicating between said non-electrically conductive surface and said electrically conductive surface of said annular frame;
   an annular frame channel circumferentially disposed in said annular frame between said non-electrically conductive surface and said electrically conductive surface; and
   an electrically conductive element disposed in said annular frame channel, said electrically conductive element electrically connected to said electrically conductive surface; and
   a power source switchably connected to said electrically conductive element which delivers a current in a range of about 0 mA to about 100 mA.

7. The nerve stimulation system of claim 6, wherein said current is selected from the group consisting of: about 1 mA to about 10 mA, about 5 mA to about 15 mA, about 10 mA to about 20 mA, about 15 mA to about 25 mA, about 20 mA to about 30 mA, about 25 mA to about 35 mA, about 30 mA to about 40 mA, about 35 mA to about 45 mA, about 40 mA to about 50 mA, about 45 mA to about 55 mA, about 50 mA to about 60 mA, about 55 mA to about 65 mA, about 60 mA to about 70 mA, about 65 mA to about 75 mA, about 70 mA to about 80 mA, about 75 mA to about 85 mA, about 80 mA to about 90 mA, about 85 mA to about 95 mA, and about 90 mA to about 99 mA, or combinations thereof.

8. The nerve stimulation system of claim 6, further comprising one or more breaker elements disposed between said power source and said electrically conductive element.

9. The nerve stimulation system of claim 6, wherein said power source comprises a direct current source or an alternating current source, wherein an alternating current delivered from said alternating current source converted to a direct current.

10. A nerve stimulation system, comprising:
an annular frame having a non-electrically conductive surface opposite an electrically conductive surface, each of said non-electrically conductive surface and said electrically conductive surface extending between an inner annular wall and an outer annular wall, said inner annular wall defining a frame aperture communicating between said non-electrically conductive surface and said electrically conductive surface of said annular frame; and
an annular frame channel circumferentially disposed in said annular frame between said non-electrically conductive surface and said electrically conductive surface;
an electrically conductive element disposed in said annular frame channel, said electrically conductive element electrically connected to said electrically conductive surface; and
a controller including a processor communicatively coupled to a non-transitory computer readable media containing a program executable to switchably electrically connect and disconnect said power source to said conductive element to generate a current pulse rate.

11. The nerve stimulation system of claim 10, wherein said current pulse rate occurs in a range of about 1 pulse per second to about 250 pulses per second (pps).

12. The nerve stimulation system of claim 11, wherein said current pulse rate is selected from the group consisting of: about 5 pps to about 20 pps, about 10 pps to about 30 pps, about 20 pps to about 40 pps, about 30 pps to about 50 pps, about 40 pps to about 60 pps, about 50 pps to about 70 pps, about 60 pps to about 80 pps, about 70 pps to about 90 pps, about 80 pps to about 100 pps, about 90 pps to about 110 pps, about 100 pps to about 120 pps, about 110 pps to about 130 pps, about 120 pps to about 140 pps, about 130 pps to about 150 pps, about 140 pps to about 160 pps, about 150 pps to about 170 pps, about 160 pps to about 180 pps, about 170 pps to about 190 pps, about 180 pps to about 200 pps, about 210 pps to about 230 pps, about 220 pps to about 240 pps, and about 230 pps to about 245 pps, or combinations thereof.

13. The nerve stimulation system of claim 10, wherein said program executable to electrically connect and disconnect said power source to said conductive element to generate a current pulse width.

14. The nerve stimulation system of claim 13, wherein said current pulse width occurs in a range of about 1 ms and about 250 ms.

15. The nerve stimulation system of claim 14, wherein said current pulse width is selected from the group consisting of: about 5 ms to about 20 ms, about 10 ms to about 30 ms, about 20 ms to about 40 ms, about 30 ms to about 50 ms, about 40 ms to about 60 ms, about 50 ms to about 70 ms, about 60 ms to about 80 ms, about 70 ms to about 90 ms, about 80 ms to about 100 ms, about 90 ms to about 110 ms, about 100 ms to about 120 ms, about 110 ms to about 130 ms, about 120 ms to about 140 ms, about 130 ms to about 150 ms, about 140 ms to about 160 ms, about 150 ms to about 170 ms, about 160 ms to about 180 ms, about 170 ms to about 190 ms, about 180 ms to about 200 ms, about 210 ms to about 230 ms, about 220 ms to about 240 ms, and about 230 ms to about 245 ms, or combinations thereof.

* * * * *